(12) United States Patent
Fujita-Yamaguchi

(10) Patent No.: US 7,329,745 B2
(45) Date of Patent: Feb. 12, 2008

(54) SINGLE-CHAIN ANTIBODIES AGAINST HUMAN INSULIN-LIKE GROWTH FACTOR I RECEPTOR: EXPRESSION, PURIFICATION, AND EFFECT ON TUMOR GROWTH

(75) Inventor: Yoko Fujita-Yamaguchi, Duarte, CA (US)

(73) Assignee: City of Hope, Duarte, CA (US)

( * ) Notice: Subject to any disclaimer, the term of this patent is extended or adjusted under 35 U.S.C. 154(b) by 459 days.

(21) Appl. No.: 10/864,818

(22) Filed: Jun. 10, 2004

(65) Prior Publication Data

US 2005/0048050 A1 Mar. 3, 2005

Related U.S. Application Data

(63) Continuation-in-part of application No. 10/134,519, filed on Apr. 30, 2002, now abandoned, which is a continuation of application No. 09/609,776, filed on Jul. 3, 2000, now abandoned.

(60) Provisional application No. 60/211,187, filed on Jun. 13, 2000.

(51) Int. Cl.
*C07H 21/04* (2006.01)
(52) U.S. Cl. .............. 536/23.5; 530/387.3; 530/388.22
(58) Field of Classification Search ................ 536/23.5; 530/387.3, 388.22
See application file for complete search history.

(56) References Cited

OTHER PUBLICATIONS

Furlanetto et al., "Effects of Insulin-Like Growth Factor Receptor Inhibition on Human Melanomas in Culture and In Athymic Mice," *Cancer Research*, 53, 2522-2526, Jun. 1, 1993.
Arteaga et al., "Growth Inhibition of Human Breast Cancer Cells in Vitro With an Antibody Against the Type I Somatomedin Receptor," *Cancer Research*, 49, 6237-6241, Nov. 15, 1989.
Li et al., "Two New Monoclonal Antibodies Against the α Subunit of the Human Insulin-Like Growth Factor-I Receptor," *Biochemical and Biophysical Research Communications*, vol. 196, No. 1, Oct. 15, 1993, pp. 92-98.
Brünner et al., "Effect of Endocrine Therapy on Growth of T61 Human Breast Cancer Xenografts is Directly Correlated to a Specific Down-regulation of Insulin-Like Growth Factor II (IGF-II)," *Eur J Cancer*, vol. 29A, No. 4, pp. 562-569, 1999.
Gura, T., Systems for identifying drugs are often faulty, Science, vol. 278, 1997, pp. 1041-1042.
Jain, R.K., Barriers, to drug delivery in solid tumors, Scientific American, vol. 271, 1994, pp. 58-65.
Curti, B.D., Physical barriers to drug delivery in tumors, Critical Reviews in Hematology/Oncology, vol. 14, 1993, 29-39.
Bergers, G., et al., Extrinsic regulators of epithelial tumor progression: metalloproteinases, Current Opinion in Genetics & Development, vol. 10, 2000, pp. 120-127.
Szollosi, J., et al., ERBB-2 (HER2/neu) gene copy No., p185-HER-2 overexpression, an intratumor heterogeneity in human breast cancer, Cancer Research, vol. 55, No. 22, 1994, pp. 5400-5407.
Strobel, T., et al., Beta 1-integrins partly mediate binding of ovarian cancer cells to peritoneal mesothelium in vitro, Gynecologic Oncology, vol. 73, No. 3, 1999, pp. 362-367.
Ezeh, P.I. et al., Differential activation of ErbB receptors in the rat olfactory mucosa by transforming growth factor-alpha and epidermal growth factor in vivo, Journal of Neurology, vol. 37, No. 2, 1998, pp. 199-210.
Lewis, G.D., et al., Differential responses to human tumor cell lines to anti-p185HER2 monoclonal antibodies, Cander Immunology Immunotherapy, vol. 37, No. 4, 1993, pp. 255-263.
Stancovski, I., et al., Mechanistic aspects of the opposing effects of monoclonal antibodies of the ERBB2 receptor in tumor growth, Proceedings of the National Academy of Sciences USA, vol. 88, 1991, pp. 8691-8695.

*Primary Examiner*—Stephen L. Rawlings
(74) *Attorney, Agent, or Firm*—Rothwell, Figg, Ernst & Manbeck

(57) ABSTRACT

A method of inhibiting the growth of hormone dependent tumor cells in a mammal comprises administering to said mammal an insulin-like growth factor receptor (IGF-IR) recombinant antibody, wherein said antibody can be a single-chain recombinant antibody, which can be humanized, capable of blocking agonist interaction with the IGF-IR.

2 Claims, 8 Drawing Sheets

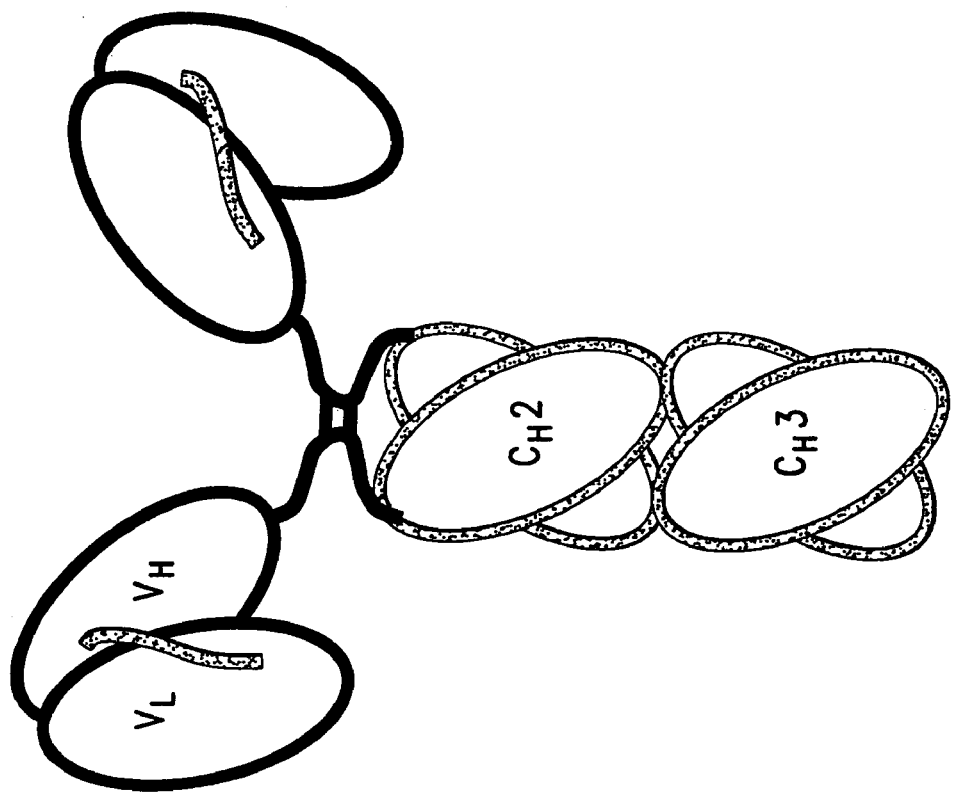
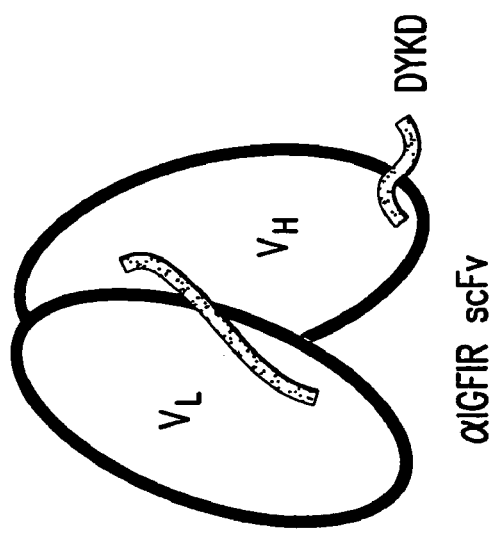

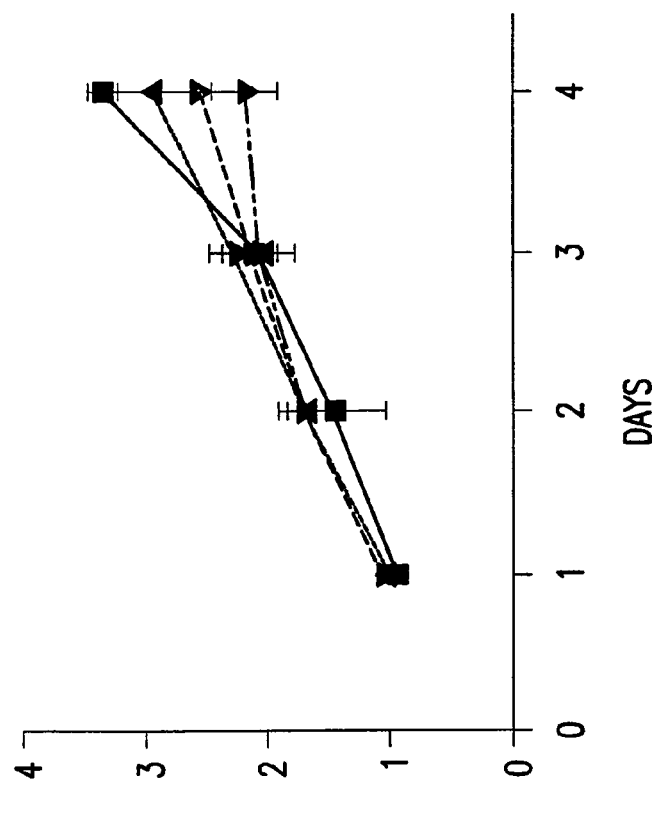
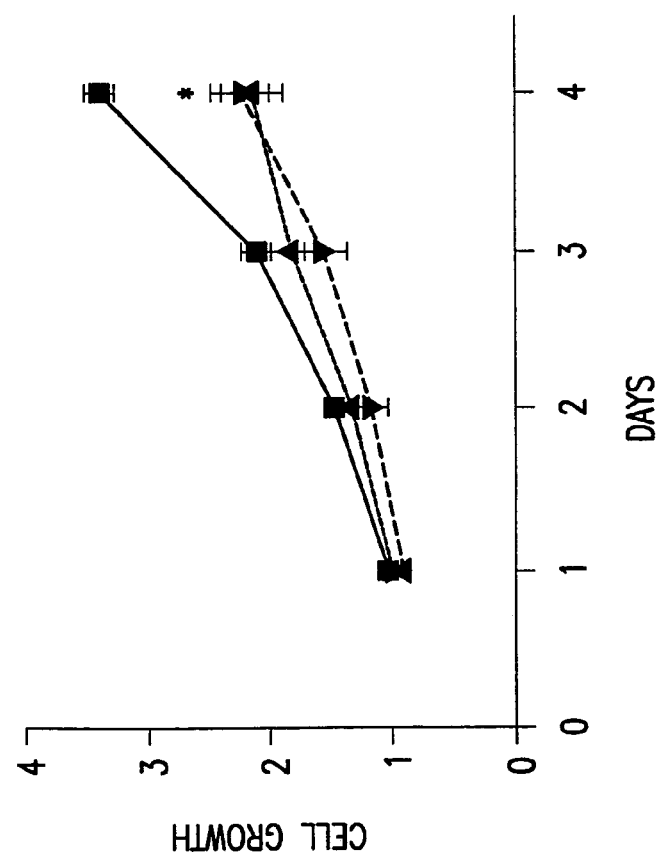
FIG. 3A
FIG. 3B

```
  1  DIVMTQSHKF MSTSVGDRVN ITCKASQDVN TAVAWYQQKP GQSPKLLIYW

51  ASTRHTGVPD RFTGSGSGTD FTLTISSVQA EDLTLYYCHQ HYTTPYTFGG

101  GTNLEIKGGG GSGGGSGGGG SGGGSEVKVV ESGGGLVKPG GSLKLSCAAS

151  GFTFSIYAMS WVRQTPEKKL EWVASISNGG TTYYPDSVKG RFTISRDNAR

201  NILYLQMNSL RSEDTAMYYC ARTFYYSFPR AMDYWGQGTS VTVSS
```

V_L
CDR1: KASQDVN TA
CDR2: WASTRHT
CDR3: HQ HYTTPYT

V_H
CDR1: IYAMS
CDR2: SISNGG TTYYPDSVKG
CDR3: TFYYSFPR AMDY

Fig. 7

```
  1 GACATTGTGA TGACCCAGTC TCACAAATTC ATGTCCACAT CGGTAGGAGA

51 CAGGGTCAAC ATCACCTGCA AGGCCAGTCA GGATGTGAAT ACTGCTGTGG

101 CGTGGTATCA ACAAAAACCA GGGCAATCTC CTAAACTCCT GATTTACTGG

151 GCATCCACCC GGCACACTGG AGTCCCTGAT CGCTTCACAG GCAGTGGATC

201 TGGGACAGAT TTTACTCTCA CCATCAGCAG TGTGCAGGCT GAAGACCTGA

251 CACTTTATTA CTGTCAGCAA CATTATAGCA CTCCGTACAC GTTCGGAGGG

301 GGGACCAATC TGGAAATAAA AGGCGGAGGC GGTAGCGGCG GTGGTTCAGG

351 AGGTGGCGGC AGTGGTGGAG GATCTGAAGT AAAAGTGGTG GAATCTGGGG

401 GAGGCTTAGT GAAGCCTGGA GGGTCCCTGA AACTCTCCTG TGCAGCCTCT

451 GGATTCACTT TCAGTATCTA TGCCATGTCA TGGGTTCGCC AGACTCCAGA

501 GAAGAAACTG GAGTGGGTCG CATCCATTAG TAATGGTGGT ACCACCTACT

551 ATCCAGACAG TGTGAAGGGC CGATTCACCA TCTCCAGAGA TAATGCCAGG

601 AACATCCTGT ACCTGCAAAT GAACAGTCTG AGGTCTGAGG ACACGGCCAT

651 GTATTACTGT GCAAGGTACC TCTACTATAG TTTTCCCGA GCTAGGACT

701 ACTGGGGTCA AGGAACCTCG GTCACCGTCT CCTCA
```

V_L
CDR
V_H
CDR

Fig. 8

SINGLE-CHAIN ANTIBODIES AGAINST HUMAN INSULIN-LIKE GROWTH FACTOR I RECEPTOR: EXPRESSION, PURIFICATION, AND EFFECT ON TUMOR GROWTH

This application is a continuation-in-part of U.S. application Ser. No. 10/134,519, filed Apr. 30, 2002, now abandoned which is a continuation of U.S. application Ser. No. 09/609,776, filed Jul. 3, 2000, now abandoned which claims priority from provisional application No. 60/211,187, filed Jun. 13, 2000. Each of these applications are incorporated by reference into this application in its entirety.

FIELD OF THE INVENTION

The present invention is in the field of methods for treatment of hormone dependent cancers.

BACKGROUND OF THE INVENTION

All references cited herein are incorporated by reference into this application in their entirety.

Insulin and Insulin-like Growth Factors stimulate the growth of human breast cancer cells in vitro. The Insulin-like Growth Factors I (IGF-I) and II (IGF-II) interact with cell surface receptors eliciting their cellular response. The IGF-I receptor (IGF-R) is the cell surface receptor for IGF-I having high binding affinity for this growth factor. However, IGF-R is also thought to have a high binding affinity for IGF-II. Interaction of either of these two growth factors to the IGF-R elicits intracellular responses through protein tyrosine phosphorylations, which can be blocked through the inhibition of the interaction of either IGF-I or IGF-II to the receptor.

These intracellular responses of IGF-IR signaling are implicated in the inducement of cell growth, proliferation and anti-apoptosis. It has been shown that the IGF-IR can not only induce normal cell growth but also induces tumor cell growth in both breast cancer and prostate cancer. In addition, the anti-apoptotic activity of IGF-IR protects cancerous tumor cells from chemotherapeutic treatments in breast cancers.

Therefore, a need exists for a method of inhibiting IGF-IR in order to inhibit tumor cell growth and increase sensitivity to chemotherapeutic agents. The activity of the IGF-IR can be inhibited by various methods. One of these methods comprises inhibiting the activation of the IGF-IR by preventing binding of agonist such as IGF-I or IGF-II. This can be achieved by blocking the IGF-IR binding site with antagonists.

Antibodies can be effective antagonists in inhibiting the interaction of the IGF-IR with IGF-I or IGF-II. αIR-3 (Arteaga, C. L. and Osborne, C. K.; Cancer Research 49, 6237-6241, 1989) is an antibody with high affinity for the IGF-IR and has been found to inhibit the interaction of IGF-I with the IGF-IR. In in vitro experimentation this murine antibody has been found to inhibit the growth of various tumor cells from breast cancer cell lines. In various tumor cells (MCF-7, MDA-231, ZR75-1, and HS578T) this αIR-3 could inhibit the IGF-I mediated DNA synthesis in vitro. However, in estrogen dependent tumor cells, such as MCF-7, ZR75-1 and T47D, the inhibition with αIR-3 of the IGF-IR in vivo failed to block estrogen stimulated DNA synthesis or proliferation. In contrast, in T61 tumor cells the αIR-3 antibody could inhibit tumor cell growth in vivo when used in combination with down-regulation of IGF-II synthesis by simultaneous treatment with estradiol and tamoxifen. It appears that αIR-3 is a better antagonist for IGF-I blockage compared to its ability to inhibit interaction of IGF-II with IGF-IR.

Another murine antibody against the α-subunit of IGF-IR, 1H7 (Li S. et al; Biochemical and Biophysical Research Communications, 196, 92-98, 1993), has shown good results in inhibiting the activation of IGF-IR. In in vitro experimentation with NIH3T3 cells over-expressing human IGF-IR the 1H7 antibody inhibits basal, IGF-I or IGF-II stimulated DNA synthesis. A second antibody raised against the IGF-IR α-subunit, 2C8, however, is unable to block IGF-IR activation by either IGF-I or IGF-II while having binding affinities for the receptor.

While these two murine antibodies, αIR-3 and 1H7, have shown results in inactivation of the IGF-IR in vitro, their ability to inhibit estrogen dependent tumor cell growth in vivo is limited. Furthermore, the monoclonal murine antibodies have their obvious disadvantages in their use for human treatment or other mammals. In addition, their relative complexity limits the ability to manipulate the antibodies to optimize their use in the treatment of mammalian hormone dependent cancers. Accordingly, improvements are sought.

SUMMARY OF THE INVENTION

In accordance with the present invention, a method of inhibiting the growth of hormone dependent tumor cells in a mammal comprises administering to said mammal an anti insulin-like growth factor I receptor (IGF-IR) recombinant antibody. In a preferred embodiment, the method comprises administering a single chain antibody (scFv). In a further preferred embodiment the method comprises administering a chimeric single chain antibody in which a constant domain has been linked to the single chain antibody.

There also is provided a novel IGF-IR antagonist comprising a recombinant antibody which blocks agonist interaction with the IGF-IR. The antibody comprises antigen binding portions that have the specificity of the antigen binding sites of the murine 1H7 antibody. The recombinant antibody can be a single chain or double chain antibody. In one embodiment of the invention, the antibody is in the form of a novel chimeric single-chain antibody against IGF-IR.

In a preferred embodiment of the invention, the antibody is in the form of the single chain recombinant antibody of SEQ ID NO:1.

BRIEF DESCRIPTION OF THE FIGURES

FIG. 1. This figure is a schematic representation of soluble forms of anti (human insulin-like growth factor I receptor) single-chain antibodies (αIGF-IR scFvs). A is a single-chain antibody (αIGF-IR scFv). B is a chimeric αIGF-IR scFv-Fc [C-terminal tag: SEQ ID NO: 22].

FIG. 3. This figure illustrates the effects of αIGF-IR scFv-Fc and 1H7 on cell growth. NIH3T3 cells over-expressing IGF-IR were cultured in the absence (■), or presence of 10 nM (▲), 100 nM (▼) or 1000 nM (♦) 1H7 (A) or αIGF-IR scFv-Fc (B).

FIG. 7. This figure shows the amino acid sequence of SP-3b1, a soluble single chain recombinant antibody, the amino acid sequence of which is comparable to the amino acid sequence of 1H7, (SEQ ID No:1), including the CDRs in both the VL and VH domains of the single chain recombinant antibody (SEQ ID NOs: 6-11, respectively).

FIG. 8. This figure shows the nucleic acid sequence of SP-3b1, a soluble single chain recombinant antibody, the amino acid sequence of which is comparable to the amino acid sequence of 1H7, (SEQ ID NO:2), including the regions coding for the CDRs of both the $V_L$ and $V_m$ domains.

DETAILED DESCRIPTION OF THE INVENTION

Figure 2A:
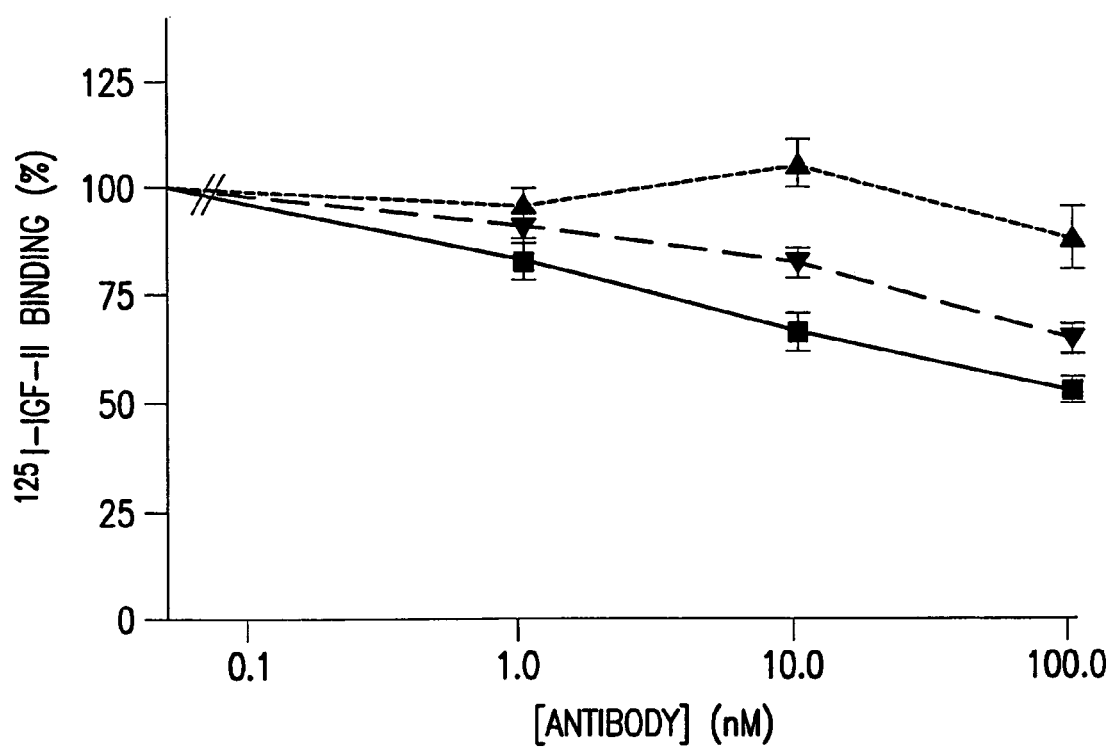
FIG. 2. This figure illustrates the effects of αIGF-IR scFv-Fc and mAb on $^{125}$I-IGF-II (A) and $^{125}$I-IGF-I (B) binding to purified human IGF-1 receptor. The binding activity is calculated as the percentage IGF-binding in the absence of antibodies, and expressed as average ±SD of four independent experiments for A or seven independent experiments for B, except that two control experiments with 2C8 mAb were performed for B. Antibodies used are αIGF-IR scFv-Fc (▼), 1H7 (■), and control 2C8 (▲).

The present invention provides a method of inhibiting hormone dependent tumor growth by blocking the activation of the Insulin-like Growth Factor I receptor (IGF-IR). This blockage can be accomplished by exposing hormone dependent tumor cells to an antagonist of IGF-IR. Inhibition of IGF-IR can lead to a decrease in cell growth and can also render the hormone dependent tumor cells more susceptible to therapeutic agents. Alternatively, the antagonist interaction with IGF-IR, inhibiting the activation of the receptor, can lead to apoptosis of the hormone dependent tumor cells.

Therefore, the invention provides a method of treatment of mammals suffering from hormone dependent tumor cell growth by administering to the mammal an anti-IGF-IR recombinant antibody. Preferably the invention provides for a treatment of mammals suffering from estrogen dependent cancer, such as breast cancer. In addition, the treatment comprises administering to said mammal an anti-IGF-IR recombinant antibody in combination with one or more therapeutic agents, such as tamoxifen, which are effective in reducing the growth of hormone-dependent tumors.

In a preferred embodiment of the invention the anti-IGF-IR antibody is a recombinant antibody wherein the antigen binding portions of the antibody are comparable to the antigen binding portions of murine antibody 1H7. Comparable antigen binding portions are ones in which the amino acid sequences have the binding specificity of the amino acid sequence of the antigen binding portions of the murine antibody 1H7. The CDRs within the binding portion have at least 90% identity to the corresponding CDR of 1H7, preferably 95% identity and most preferably full identity. Particularly preferred is a single chain recombinant antibody, such as the αIGF-IR scFv or αIGF-IR scFv-Fc antibody comprising antigen binding portions comparable to the antigen binding portions of murine antibody 1H7, or even more preferred is the single chain recombinant antibody of SEQ ID NO:1. The single chain antibodies are advantageous because of the relative ease in their expression, purification and manipulation. The expression of such antibodies in expression systems makes them more susceptible to large scale production and purification. In addition, manipulation of such single chain antibodies may consist of altering such antibodies to covalently attach other therapeutic agents. Such agents can, for example, include toxins, enzymes, or radionucleotides. The recombinant single chain antibody conjugated with such agents can block IGF-IR induced tumor cell growth and target such agents to said tumor cells which have been made more susceptible to apoptosis by the inhibition of IGF-IR.

The single chain antibody comprises at least an Fv domain capable of blocking IGF-IR interaction with IGF-I or IGF-II. The IGF-IR scFv comprises both the antigen binding region of a light chain variable domain, $V_L$, and the antigen binding region of a heavy chain variable domain, $V_H$, coupled by a short linker peptide. In a preferred embodiment, the $V_L$ domain and the $V_H$ domain are derived from the 1H7 antibody against the α-subunit of IGF-IR. The IGF-IR scFv can be tagged with a short peptide such as the FLAG epitope to facilitate purification of the soluble IGF-IR scFv from the medium of the expression system. The DNA coding for the $V_L$ and $V_H$ domains are obtainable by sequencing said domains from a parental antibody, in a preferred embodiment said parental antibody being 1H7. A recombinant DNA then can be constructed comprising, in order, coding sequences for the N-terminal signal peptide, the antigen binding region of the $V_L$ domain, a linker peptide, the antigen binding region of the $V_H$ domain and a C-terminal tag peptide for purification and identification. Said genetically engineered antibody can be expressed in myeloma or bacterial cell expression systems. The monovalent recombinant single chain antibody IGF-IR scFv can be purified from the medium of said expression system by conventional protein purification methods, such as, for example, affinity chromatography.

The linker peptide is chosen based upon known structural and conformational information of peptide segments and is selected so that it will not interfere with the tertiary structure of the single chain antibody and its uses. Typically, a linker of between about 6 and 50 amino acids is preferred for ease and economics of preparation.

Figure 2B:
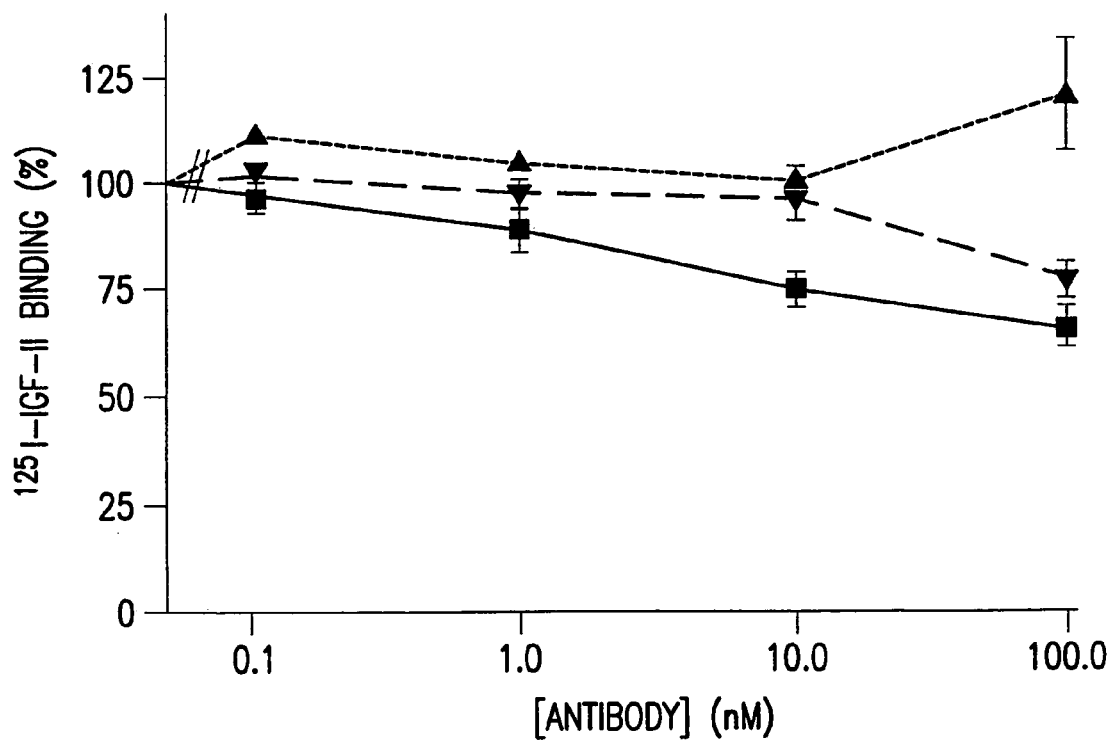

One such single chain recombinant antibody comprising antigen binding portions comparable to the antigen binding portions of murine antibody 1H7 is the peptide with the binding specificity of the sequence shown in SEQ ID NO:1 shown in FIG. 1. FIG. 2 shows the nucleic acid sequence encoding this single chain recombinant antibody. The single chain recombinant antibody of SEQ ID NO:1 comprises a $V_L$ domain (SEQ ID NO:3) and a $V_H$ domain (SEQ ID NO:4) which are linked by the linker peptide

```
GGGGSGGGSGGGGSGGGS.        (SEQ ID NO: 5)
```

Each of these domains ($V_L$ and $V_H$) contain three complimentarity determining regions (CDRs) responsible for antigen recognition. The three CDRs of the $V_L$ domain KASQD-VNTA (SEQ ID NO:6), WASTRMMT (SEQ ID NO:7), and HQHYTTPYT (SEQ ID NO:8), are designated CDR1$_L$, CDR2$_L$ and CDR3$_L$ respectively. The three CDRs of the V$_H$ domain, IYAMS (SEQ ID NO:9), SISNGGTTYYPDSVKG (SEQ ID NO:10), and TFYYSFPRAMDY (SEQ ID NO:11) are designated CDR1$_H$, CDR2$_H$, and CDR3$_H$ respectively.

In one embodiment of the invention the soluble IGF-IR scFv is a chimeric antibody which further comprises an Fc domain. In this embodiment, the recombinant DNA will comprise the coding sequence of IGF-IR scFv minus the C-terminal tag peptide, coupled to a coding sequence for an Fc domain. Desirably, the Fc domain comprises the C$_{H2}$ and C$_{H3}$ regions of an antibody heavy chain constant domain. The recombinant DNA can be expressed in a myeloma or bacterial expression system in accordance with conventional techniques and said single-chain antibody IGF-IR scFv-Fc can be purified using conventional protein purification methods. The IGF-IR scFv-Fc exists preferably in its divalent form. The IGF-IR scFv-Fc can comprise a humanized form of the IGF-IR scFv, such as, for example, by using a coding sequence of a human Fc domain when constructing the recombinant DNA. Said single chain antibodies (IGF-IR scFv or IGF-IR scFv-Fc) subsequently can be modified, if desired, and attached to other therapeutic agents.

To treat mammals suffering from hormone dependent cancer, preferably from estrogen dependent breast cancer, the recombinant single-chain antibodies (IGF-IR scFv or IGF-IR scFv-Fc) can be administered in a pharmaceutically acceptable composition as the sole therapeutic or in combination with one or more other therapeutic agents, such as tamoxifen, which are effective in reducing hormone-dependent tumor cell growth. The tamoxifen or other therapeutic agent can be administered in accordance with conventional therapeutic methods, such as parenteral or subcutaneous administration. Administration of said recombinant single chain antibodies can be used as a method of inhibiting tumor cell growth in vivo or to induce susceptibility of said tumor cells to therapeutic agents.

In light of the preceding description, one skilled in the art can use the present invention to its fullest extent. The following examples, therefore, are to be construed as illustrative only and not limiting in relation to the remainder of the disclosure.

EXAMPLE 1

Cloning of 1H7 Variable Domains by RT-PCR.

Heavy and light chains of mouse monoclonal antibody 1H7 (Li, S. et al; *Biochemical and Biophysical Research Communications*, 196, 92-98, 1993) were separated by sodium dodecyl sulfate/polyacrylamide gel electrophoresis (SDS-PAGE; 12.5% polyacrylamide gel), under reducing conditions, blotted onto a polyvinylidene difluoride membrane, and subjected to N-terminal amino acid sequence determination by Edman degradation. Degenerate oligonucleotides, used as upstream primers, were synthesized on the N-terminal sequences of the heavy and light chains of 1H7 while the constant region oligonucleotides for the downstream primers were designed and synthesized according to the published nucleotide sequences. Primers (Table 1) containing the EcoRI site were used to amplify the heavy- and light-chain variable regions (V$_H$ and V$_L$, respectively) from 1H7 poly(A) rich mRNA by reverse transcriptase polymerase chain reaction (RT-PCR). PCR products were ligated into the EcoRI site of pBleuscriptII SK. *Escheria coli* XL1-Blue was transformed with the vectors encoding PCR-generated V$_H$ and V$_L$ sequences.

The N-terminal amino acid sequences of the heavy-and light-chains of 1H7 were determined to be EVKVVESGGGLVKPG (SEQ ID: NO 12) and DIVMTQSHKFMSTSV (SEQ ID: NO: 13) respectively.

TABLE 1

Primers for PCR amplification of variable regions of heavy and light chains of 1H7

| Light-chain primers | | | | | | | | | |
|---|---|---|---|---|---|---|---|---|---|
| Amino Acid | | 1 | 2 | 3 | 4 | 5 | 6 | | |
| | | Asp | Ile | Val | Met | Thr | Gln | | [SEQ IN NO: 14] |
| 5'end primer | gggaattc | GAC | ATT | GTG | ATG | ACC | CAA 3' | | [SEQ IN NO: 15] |
| | | T | C | C | | A | G | | |
| | | | | | | T | | | |
| C-region amino acid | | Ser | Ile | Phe | Pro | Pro | Ser | | [SEQ IN NO: 16] |
| C-region primer | 5' | TCC | ATC | TTC | CCA | CCA | TCC | gaattccg 3' | [SEQ IN NO: 17] |
| Heavy-chain primers | | | | | | | | | |
| Amino Acid | | 1 | 2 | 3 | 4 | 5 | 6 | | |
| | | Glu | Val | Lys | Val | Val | Glu | | [SEQ IN NO: 18] |
| 5'end primer | gggaattc | GAA | GTA | AAA | GTA | GTA | GAA 3' | | [SEQ IN NO: 19] |
| | | G | C | G | C | C | G | | |
| | | G | | | G | G | | | |
| C-region amino acid | | Val | Tyr | Pro | Leu | Ala | Pro | | [SEQ IN NO: 20] |
| C-region primer | 5' | GTC | TAT | CCA | CTG | GCC | CCT | gaattccg 3' | [SEQ IN NO: 21] |

EXAMPLE 2

Design of αIGF-IR Antibodies.

Two soluble forms of 1H7-based αIGF-IR antibodies, scFv and scFv-Fc, were designed as schematically presented in FIG. 3. ScFv is a monovalent antibody and has an expected M$_r$ of 27 kDa. ScFv-Fc is a divalent antibody that contains the human IgG1 Fc domain and has an expected M$_r$ of 120 kDa.

The gene encoding the αIGF-IR scFv was constructed using the N-terminal signal peptide derived from the mT84.66 light chain, V$_L$ DNA, an oligonucleotide encoding the linker peptide (GGGGSGGGS)$_2$ (SEQ ID NO: 5), V$_H$ DNA, and a C-terminal tag (including DYKD; SEQ ID NO: 22]), and assembled using splice-overlap extension PCR.

The resulting DNA encoding αIGF-IR scFv is shown in FIG. 2 (SEQ ID NO: 2). The αIGF-IR scFv construct was cloned into pcDNA3 (Invitrogen, San Diego, Calif.), containing the cytomegalovirus promoter and neo$^r$ selection marker (pcDNA/αIGF-IR scFv).

To construct the gene encoding αIGF-IR scFv-Fc, a SalI fragment containing the human IgG1 Fc (cDNA clone from Dr. J. Schlom, Laboratory of Tumor Immunology and Biology, division of Cancer Biology and Diagnosis, NCI, Bethesda, Md.) was inserted into the unique XhoI site of pcDNA/αIGF-IR scFv. The HindIII fragment encoding αIGF-IR scFv-Fc, isolated from the pcDNA/αIGF-IR scFv-Fc plasmid, was inserted into the HindIII site of pEE12-1. This plasmid encodes a glutamine synthase gene that provides a selection system for myeloma NS0 cells in L-glutamine-deficient selection medium.

EXAMPLE 3

Cell Culture, Transfection and Purification of αIGF-IR scFv or αIGF-IR scFv-Fc.

Murine myeloma Sp2/0 cells were transfected with pcDNA/αIGF-IR scFv by electroporation, and incubated at 37° C. for 3 days in a humidified 5% CO$_2$ atmosphere. On day 4, cells were collected, counted and placed in 24-well plates (10$^5$ cells/well) in regular medium containing 400 μg/ml G418. Murine myeloma NS0 cells were grown in selective medium consisting of L-glutamine-free Celltech DME (JRH Biosciences, Lenexa, Kans.), dialyzed fetal calf serum (Gibco/BRL, Gaithersburg, Md.), and glutaminase synthase supplement (JRH Biosciences, Lenexa, Kans.). Murine myeloma NS0 cells were stably transfected with pEE12-1/αIGF-IR scFv-Fc by electroporation and transferred to non-selective culture medium in a 96-well plate (50 μl/well), and incubated overnight. The next day 150 μl of selection medium was added to each well, and the cells were incubated for three weeks until discrete surviving colonies appeared.

To purify αIGF-IR scFv by affinity chromatography, 150 ml of conditioned medium (CM), collected from Sp2/0 cells, were applied to 6 ml αFLAG M2 mAb (Eastman Kodak Co., Rochester, N.Y.) conjugated to Sepharose 4B (0.2 mg/ml gel), and αIGF-IR scFv-Fc was eluted from the column with FLAG peptide. Eluates were concentrated and dialyzed, using an Ultrafree-4 spin column (Millipore, Bedford, Mass.). Based on the recovery of approximately 4 μg of αIGF-IR scFv protein from purifying 150 ml CM, the level of αIGF-IR scFv expression was estimated to be approximately 20 ng/ml CM.

To purify αIGF-IR scFv-Fc approximately 40 ml cell culture supernatants collected from αIGF-IR scFv-Fc expressing NS0 transfectants were adjusted to pH 8.0 by adding 1/20 volume 1.0M TRIS (pH 8.0), and passed through a protein-A-Sepharose CL 4B column. αIGF-IR scFv-Fc was eluted from the column with 100 mM glycine buffer pH 3.0, collected in 1.5 ml conical tubes containing 1/10 volume 1M TRIS (pH 8.0). The estimated expression level of αIGF-IR scFv-Fc in this expression system ranged between 45 μg/ml and 85 μg/ml.

EXAMPLE 4

Inhibition of Agonist Binding to Purified IGF-IR by 1H7 and αIGF-IR scFv-Fc.

The affinity constants of 1H7 (10$^9$ M$^{-1}$) and αIGF-IR scFv-Fc (10$^8$ M$^{-1}$) for IGF-IR were determined using a BIAcore instrument (BIAcore Inc., Piscataway, N.J.). Analytes, at various concentrations, were passed over IGF-IR-immobilized chips (0.3 μg/chip) at a flow rate of 5 μl/min.

Figure 4:
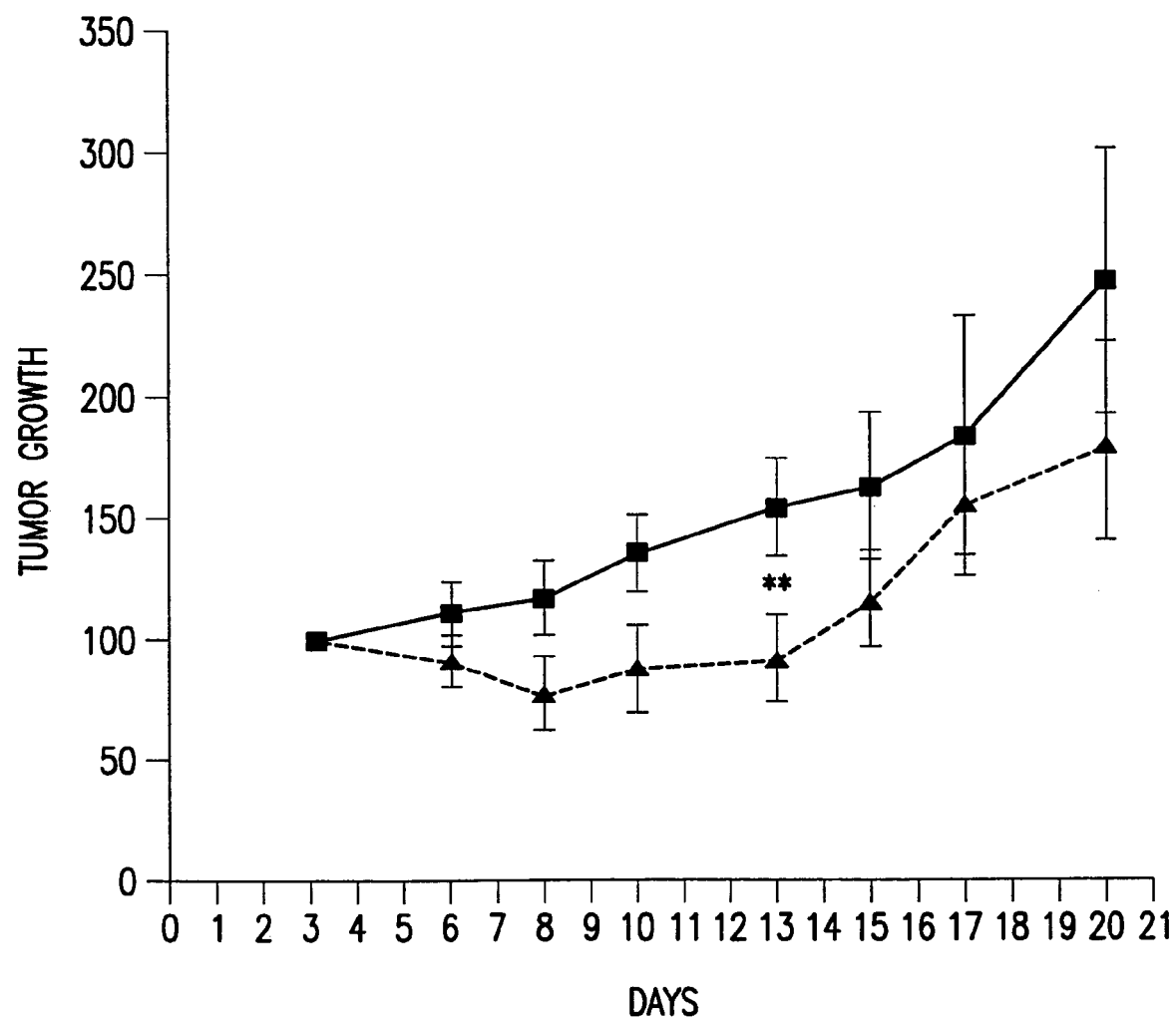
FIG. 4. This figure illustrates the effects of MCF-7 tumor cell growth in nude mice in the absence (■) or presence (▲) of αIGF-IR scFv-Fc.

The in vitro potency of inhibition of purified IGF-IR by αIGF-IR scFv-Fc for both IGF-I and IGF-II binding is seen in FIG. 4.

EXAMPLE 5

Effect of αIGF-IR scFv-Fc on Cell Growth.

Figure 5:
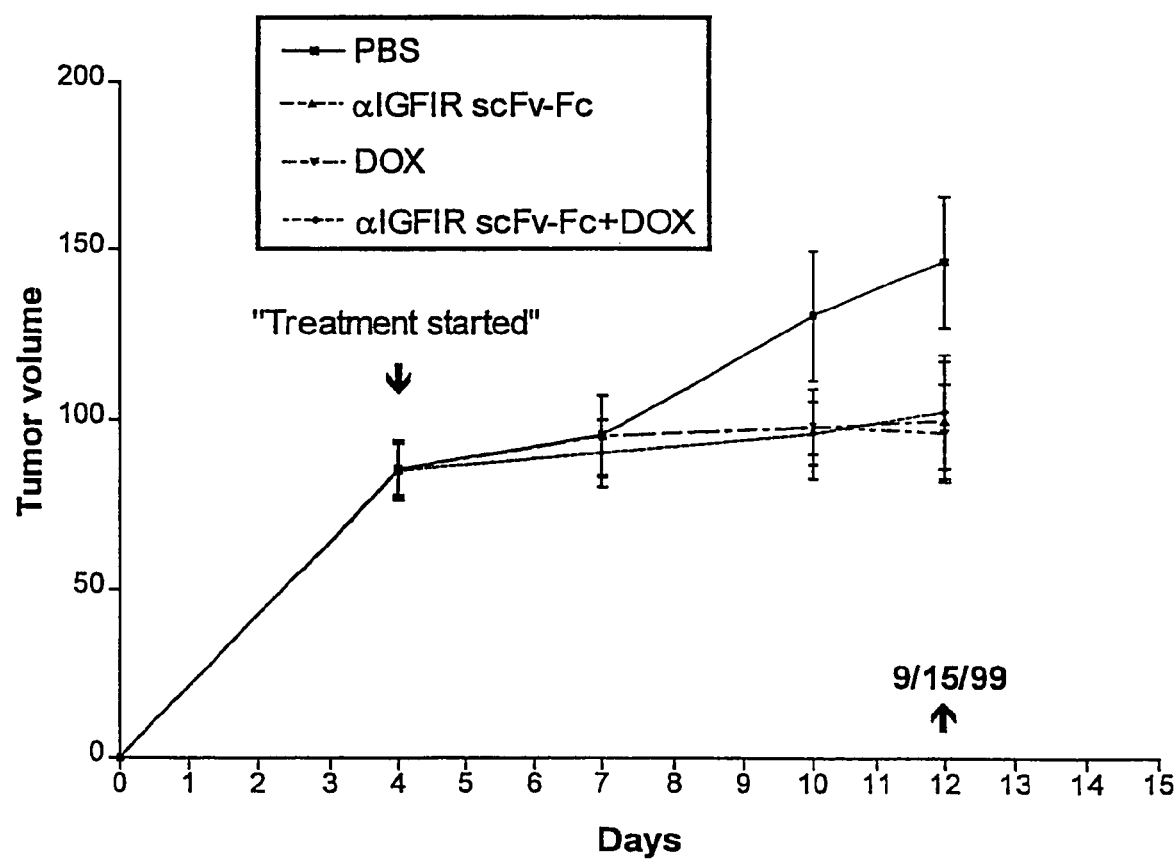
FIG. 5. This figure illustrates the effects of αIGF-IR scFv-Fc on MCF-7 tumor cell growth in vivo in the presence or absence of the anti-neoplastic agent Doxorubicin. On day 0 MCF-7 cells were implanted in the mouse followed by a treatment of PBS (control)(■), αIGF-IR scFv-Fc (▲), Doxorubicin (▼) or αIGF-IR scFv-Fc+Doxorubicin (♦) beginning at day 4.

Using the MTT method the effect of extracellular addition of αIGF-IR scFv-Fc or 1H7 on cell growth was determined on NIH3T3 cells over expressing IGF-IR. Cell growth was significantly inhibited after four days of treatment with 10 nM or 100 nM 1H7 mAb, see FIG. 5. Also, after 4 days of treatment with αIGF-IR scFv-Fc cell growth appeared to be inhibited in a dose dependent manner as is shown in FIG. 5.

EXAMPLE 6

Effect of αIGF-IR scFv-Fc on Tumor Growth In vivo.

The human breast MCF-7 cell line was obtained from American Type Culture Collection (Rockville, Md.). MCF-7 cells were cultured in Dulbecco's modified Eagle's medium supplemented with 5% fetal calf serum. Female athymic mice (BALB/C nude, Charles River Facility for NCI, Frederick, Md.), 4 weeks old, that had received 0.25 mg 17β-estradiol pellet one week previously were inoculated in the flank with 10$^7$ MCF-7 cells (day 0). On day 3, intraperitoneal or subcutaneous injections near the tumor sites of αIGF-IR scFv-Fc into each of three mice (500 μg/0.1 ml phosphate buffered saline, PBS/mouse, twice a week) was started, and continued for two weeks.

Figure 6:
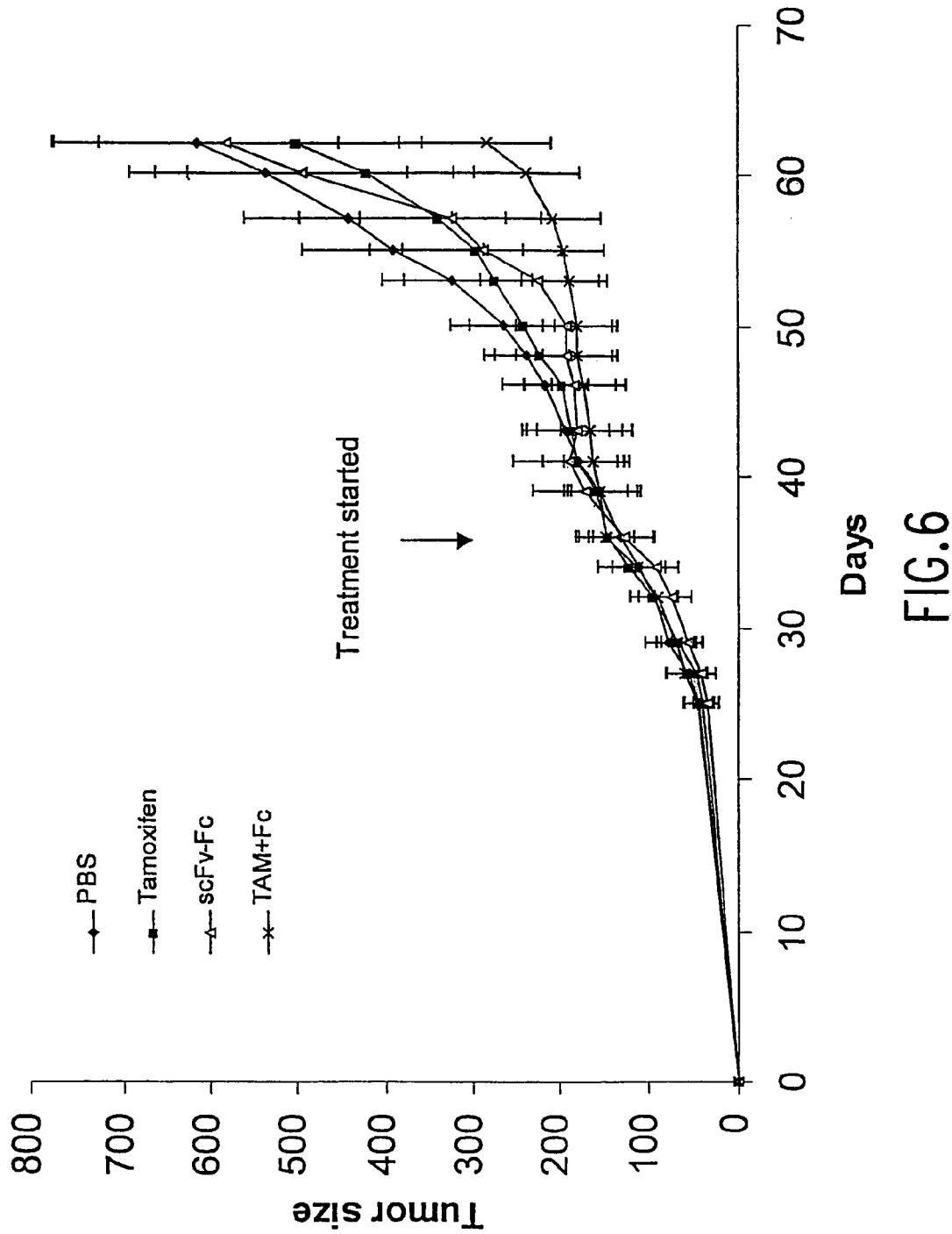
FIG. 6. This figure illustrates the effects of αIGF-IR scFv-Fc on T61 tumor cell growth in vivo in the presence or absence of the estrogen antagonist Tamoxifen (TAM). On day 36 following implantation of T61 tumor cells the mice were treated with PBS (control) (●), αIGF-IR scFv-Fc (Δ), tamoxifen (■) or αIGF-IR scFv-Fc+tamoxifen (*).

The recombinant single chain antibody αIGF-IR scFv-Fc inhibits MCF-7 tumor cell growth in athymic mice. As shown in FIG. 6, inhibition of tumor cell growth is significant, although, the results for individual mice varied. In several mice MCF-7 tumor cell growth was completely suppressed from day 3 to day 17, and in one mouse the tumor disappeared.

EXAMPLE 7

Effect of αIGF-IR scFv-Fc in Combination with Anti-Neoplastic Agent Doxorubicin (DOX) on Tumor Growth In vivo.

In combination with Doxorubicin (DOX), αIGF-IR scFv-Fc inhibits tumor cell growth, as shown in FIG. 7. Female athymic mice were treated similarly as described above in example 6, with the exception that the pellet with which the mice were inoculated contained 0.72 mg 17β-estradiol. The treatment of the mice was started on day 4 by either intraponeal injections of αIGF-IR scFv-Fc as in example 6 three times per week, by intraponeal injections of DOX (2 mg/kg bodyweight) once a week, or by a combination of both.

EXAMPLE 8

Effect of αIGF-IR scFv-Fc in Combination with Anti-Estrogen Agent Tamoxifen (TAM) on Tumor Growth In vivo.

In combination with the anti-estrogen drug Tamoxifen (TAM), αIGF-IR scFv-Fc inhibits T61 tumor cell growth in vivo as is shown in FIG. 8. The observed inhibition of a combination treatment in these T61 tumor cells shows a synergistic effect. Female athymic mice were inoculated with T61 tumor cells. The treatment of the mice was started on day 36 by either intraponeal injections of αIGF-IR scFv-Fc as in example 6 three times per week, by subcutaneous implantation of 5 mg of a TAM pellet, or a combination of both.

---

What is claimed is:

1. A purified nucleic acid encoding a single chain recombinant antibody comprising a $V_L$ domain comprising complementarity determining regions having the amino acid sequences set forth in SEQ ID NO: 6, SEQ ID NO: 7, SEQ ID NO: 8 and a $V_H$ domain comprising complementarity determining regions having the amino acid sequences set forth in SEQ ID NO: 9, SEQ ID NO: 10, SEQ ID NO: 11, wherein said antibody binds insulin-like growth factor I receptor.

2. The nucleic acid of claim 1, wherein the nucleic acid has the nucleic acid sequence set forth in SEQ ID NO: 2.

* * * * *

UNITED STATES PATENT AND TRADEMARK OFFICE
CERTIFICATE OF CORRECTION

PATENT NO. : 7,329,745 B2
APPLICATION NO. : 10/864818
DATED : February 12, 2008
INVENTOR(S) : Fujita-Yamaguchi It is certified that error appears in the above-identified patent and that said Letters Patent is hereby corrected as shown below:

In the specification, page 1, column 1, after the title, please add the following paragraph:

The invention described herein was made with Government support under contract number DOD (DOD Prostate Cancer Research Program) DAMD17-98-1-8579. Accordingly, the United States Government has certain rights in this invention.

Signed and Sealed this

Eighteenth Day of November, 2008

JON W. DUDAS
*Director of the United States Patent and Trademark Office*

SEQUENCE LISTING

<160> NUMBER OF SEQ ID NOS: 13

<210> SEQ ID NO 1
<211> LENGTH: 245
<212> TYPE: PRT
<213> ORGANISM: murine

<400> SEQUENCE: 1

```
Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Glu Asp Leu Thr Leu Tyr Tyr Cys His Gln His Tyr Thr Thr Pro Tyr
                85                  90                  95

Thr Phe Gly Gly Gly Thr Asn Leu Glu Ile Lys Gly Gly Gly Gly Ser
            100                 105                 110

Gly Gly Gly Ser Gly Gly Gly Gly Ser Gly Gly Gly Ser Glu Val Lys
        115                 120                 125

Val Val Glu Ser Gly Gly Gly Leu Val Lys Pro Gly Gly Ser Leu Lys
    130                 135                 140

Leu Ser Cys Ala Ala Ser Gly Phe Thr Phe Ser Ile Tyr Ala Met Ser
145                 150                 155                 160

Trp Val Arg Gln Thr Pro Glu Lys Lys Leu Glu Trp Val Ala Ser Ile
                165                 170                 175

Ser Asn Gly Gly Thr Thr Tyr Tyr Pro Asp Ser Val Lys Gly Arg Phe
            180                 185                 190

Thr Ile Ser Arg Asp Asn Ala Arg Asn Ile Leu Tyr Leu Gln Met Asn
        195                 200                 205

Ser Leu Arg Ser Glu Asp Thr Ala Met Tyr Tyr Cys Ala Arg Thr Phe
    210                 215                 220

Tyr Tyr Ser Phe Pro Arg Ala Met Asp Tyr Trp Gly Gln Gly Thr Ser
225                 230                 235                 240

Val Thr Val Ser Ser
                245
```

<210> SEQ ID NO 2
<211> LENGTH: 735
<212> TYPE: DNA
<213> ORGANISM: murine

<400> SEQUENCE: 2

```
gacattgtga tgacccagtc tcacaaattc atgtccacat cggtaggaga cagggtcaac      60
atcacctgca aggccagtca ggatgtgaat actgctgtgg cctggtatca acaaaaacca     120
gggcaatctc ctaaactcct gatttactgg gcatccaccc ggcacactgg agtccctgat     180
```

```
cgcttcacag gcagtggatc tgggacagat tttactctca ccatcagcag tgtgcaggct    240
gaagacctga cactttatta ctgtcatcaa cattatacca ctccgtacac gttcggaggg    300
gggaccaatc tggaaataaa aggcggaggc ggtagcggcg gtggttcagg aggtggcggc    360
agtggtggag gatctgaagt aaaagtggtg gaatctgggg gaggcttagt gaagcctgga    420
gggtccctga actctcctg tgcagcctct ggattcactt tcagtatcta tgccatgtca    480
tgggttcgcc agactccaga aagaaactg gagtgggtcg catccattag taatggtggt    540
accacctact atccagacag tgtgaagggc cgattcacca tctccagaga taatgccagg    600
aacatcctgt acctgcaaat gaacagtctg aggtctgagg acacggccat gtattactgt    660
gcaaggtacc ttctactata gttttccccg agctaggact actggggtca aggaaccctcg   720 gtcaccgtct cctca                                                      735

<210> SEQ ID NO 3
<211> LENGTH: 107
<212> TYPE: PRT
<213> ORGANISM: murine

<400> SEQUENCE: 3

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Glu Asp Leu Thr Leu Tyr Tyr Cys His Gln His Tyr Thr Thr Pro Tyr
                85                  90                  95

Thr Phe Gly Gly Gly Thr Asn Leu Glu Ile Lys
            100                 105

<210> SEQ ID NO 4
<211> LENGTH: 120
<212> TYPE: PRT
<213> ORGANISM: murine

<400> SEQUENCE: 4

Glu Val Lys Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Ile Tyr
            20                  25                  30

Ala Met Ser Trp Val Arg Gln Thr Pro Glu Lys Lys Leu Glu Trp Val
        35                  40                  45

Ala Ser Ile Ser Asn Gly Gly Thr Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Asn Ser Leu Arg Ser Glu Asp Thr Ala Met Tyr Tyr Cys Ala
                85                  90                  95

Arg Thr Phe Tyr Tyr Ser Phe Pro Arg Ala Met Asp Tyr Trp Gly Gln
            100                 105                 110
```

Gly Thr Ser Val Thr Val Ser Ser
        115                 120

<210> SEQ ID NO 5
<211> LENGTH: 18
<212> TYPE: PRT
<213> ORGANISM: murine

<400> SEQUENCE: 5

Gly Gly Gly Gly Ser Gly Gly Ser Gly Gly Gly Ser Gly Gly
1               5                   10                  15

Gly Ser

<210> SEQ ID NO 6
<211> LENGTH: 9
<212> TYPE: PRT
<213> ORGANISM: murine

<400> SEQUENCE: 6

Lys Ala Ser Gln Asp Val Asn Thr Ala
1               5

<210> SEQ ID NO 7
<211> LENGTH: 7
<212> TYPE: PRT
<213> ORGANISM: murine

<400> SEQUENCE: 7

Trp Ala Ser Thr Arg His Thr
1               5

<210> SEQ ID NO 8
<211> LENGTH: 9
<212> TYPE: PRT
<213> ORGANISM: murine

<400> SEQUENCE: 8

His Gln His Tyr Thr Thr Pro Tyr Thr
1               5

<210> SEQ ID NO 9
<211> LENGTH: 5
<212> TYPE: PRT
<213> ORGANISM: murine

<400> SEQUENCE: 9

Ile Tyr Ala Met Ser
1               5

<210> SEQ ID NO 10
<211> LENGTH: 16
<212> TYPE: PRT
<213> ORGANISM: murine

<400> SEQUENCE: 10

Ser Ile Ser Asn Gly Gly Thr Thr Tyr Tyr Pro Asp Ser Val Lys Gly
1               5                   10                  15

<210> SEQ ID NO 11
<211> LENGTH: 12
<212> TYPE: PRT
<213> ORGANISM: murine

<400> SEQUENCE: 11

-continued

```
Thr Phe Tyr Tyr Ser Phe Pro Arg Ala Met Asp Tyr
1               5                   10

<210> SEQ ID NO 12
<211> LENGTH: 15
<212> TYPE: PRT
<213> ORGANISM: murine

<400> SEQUENCE: 12

Glu Val Lys Val Val Glu Ser Gly Gly Gly Leu Val Lys Pro Gly
1               5                   10                  15

<210> SEQ ID NO 13
<211> LENGTH: 15
<212> TYPE: PRT
<213> ORGANISM: murine

<400> SEQUENCE: 13

Asp Ile Val Met Thr Gln Ser His Lys Phe Met Ser Thr Ser Val
1               5                   10                  15
```